(12) United States Patent
Tappehorn et al.

(10) Patent No.: US 8,448,642 B2
(45) Date of Patent: May 28, 2013

(54) MEASURING GAS SAMPLE HOLDER FOR MEASURING THE CONCENTRATIONS OF GAS COMPONENTS AND PROCESS FOR MANUFACTURING A MEASURING GAS SAMPLE HOLDER

(75) Inventors: Ludger Tappehorn, Lübeck (DE); Petrus Stephanus van Zyl, Erfstadt (DE); Chritiane Göbel, Loxstedt (DE); Jennifer Lünse, Lübeck (DE); Horst-Dieter Hattendorff, Bad Schwartau (DE)

(73) Assignee: Dräger Medical GmbH, Lübeck (DE)

( * ) Notice: Subject to any disclaimer, the term of this patent is extended or adjusted under 35 U.S.C. 154(b) by 1014 days.

(21) Appl. No.: 12/514,135

(22) PCT Filed: Nov. 2, 2007

(86) PCT No.: PCT/DE2007/001976
§ 371 (c)(1),
(2), (4) Date: Jun. 18, 2009

(87) PCT Pub. No.: WO2008/055478
PCT Pub. Date: May 15, 2008

(65) Prior Publication Data
US 2009/0320846 A1    Dec. 31, 2009

(30) Foreign Application Priority Data
Nov. 10, 2006 (DE) .......... 10 2006 052 999

(51) Int. Cl.
*A61M 16/00* (2006.01)
*A61B 5/08* (2006.01)

(52) U.S. Cl.
USPC ............. 128/204.23; 128/205.23; 600/532

(58) Field of Classification Search
USPC ............ 128/204.23, 205.23; 600/532
See application file for complete search history.

(56) References Cited

U.S. PATENT DOCUMENTS

| 4,011,859 | A |   | 3/1977  | Frankenberger |            |
|-----------|---|---|---------|---------------|------------|
| 5,067,492 | A | * | 11/1991 | Yelderman et al. | 600/532 |
| 5,095,900 | A | * | 3/1992  | Fertig et al. | 128/207.14 |
| 5,696,379 | A |   | 12/1997 | Stock         |            |
| 5,957,127 | A | * | 9/1999  | Yamamori et al. | 128/204.22 |
| 6,095,986 | A |   | 8/2000  | Braig et al.  |            |
| 6,325,978 | B1 | * | 12/2001 | Labuda et al. | 422/84  |
| 7,294,839 | B2 | * | 11/2007 | Rich et al.   | 250/343 |
| 7,335,164 | B2 | * | 2/2008  | Mace et al.   | 600/532 |

FOREIGN PATENT DOCUMENTS

| DE | 195 20 488     | 9/1996  |
| SE | WO 2004/096043 | 11/2004 |
| US | WO 2004/081612 | 9/2004  |

\* cited by examiner

*Primary Examiner* — Lynne Anderson
(74) *Attorney, Agent, or Firm* — McGlew and Tuttle, P.C.

(57) ABSTRACT

A measurement gas vessel (3) for the measurement of the concentration of gas components of a stream of breath from a patient has a thin-walled inner part (11) which has two opposite facing walls limiting the breath stream. The walls are transparent to infrared light. An outer part (10) which in the central region (7) has two recesses on opposite sides which, with the walls (16) of the inner part (11), each form a window (9). A region of the inner part (11) outside the windows (9) is thermally connected to the outer part (10), and the outer part (10) surrounds the inner part (11).

20 Claims, 3 Drawing Sheets

MEASURING GAS SAMPLE HOLDER FOR MEASURING THE CONCENTRATIONS OF GAS COMPONENTS AND PROCESS FOR MANUFACTURING A MEASURING GAS SAMPLE HOLDER

CROSS REFERENCE TO RELATED APPLICATIONS

This application is a United States National Phase application of International Application PCT/DE2007/001976 and claims the benefit of priority under 35 U.S.C. §119 of German Patent Application DE 10 2006 052 999.5 filed Nov. 10, 2006, the entire contents of which are incorporated herein by reference.

FIELD OF THE INVENTION

The present invention pertains to a measuring gas sample holder for measuring the concentration of gas components and to a process for manufacturing a measuring gas sample holder.

BACKGROUND OF THE INVENTION

Measuring means for measuring the concentration of gas components of the respiratory flow of a patient are known from clinical practice. They are used here especially in the medical method of capnometry, in which the carbon dioxide content in the air expired by a patient is measured and monitored. The respiration can be adapted to the patient relatively well on the basis of the carbon dioxide concentration. It is also possible to recognize early whether an endotracheal tube is in the correct position and whether the patient's metabolic situation is correct. The latter point makes it possible to perform interventions early in case of certain complications, such as malignant hyperthermia, or it yields a reference value for the effectiveness of resuscitation.

The mainstream method, in which a measuring gas sample holder is provided in a respiratory flow between the respiratory tract of a patient and a respirator, is preferably used to measure the concentration of gas components of the respiratory flow. An infrared measuring method, which involves radiation through the tidal volume flow, as it is disclosed, for example, in DE 19 520 488 C1, in which the concentration-dependent absorption of the infrared radiation emitted by an infrared radiation source is detected after passing through the respiratory flow in the measuring gas sample holder for a wavelength characteristic of a certain gas, such as $CO_2$, is used for this. The concentration of the gas determined can be determined by calculation from the measured signal received. The measuring gas sample holder has for this two opposite windows, which are arranged at right angles to the direction of flow and through which infrared light is sent.

A measuring gas sample holder for measuring the concentration of gas components of the breathing air, in which the measuring gas sample holder housing and the measuring gas sample holder windows, through which an infrared light is sent, are manufactured separately, is known from WO 2004/096043 A1. The measuring gas sample holder windows are manufactured according to an injection molding process and are subsequently connected to the measuring gas sample holder housing according to a suitable bonding method. A defined distance between the measuring gas sample holder windows is essential for the calculation of the concentration of a certain gas. The distance defines an inner volume of the measuring gas sample holder, which volume affects the calculation of the concentration of the gas components of the breathing air. Due to the bonding in the measuring gas sample holder windows, the distance may deviate from a defined value and inaccuracies may consequently develop in the calculated concentration values.

Furthermore, the measuring gas sample holder windows have a very small wall thickness. Even though a small wall thickness of the measuring gas sample holder windows is advantageous for the transmission characteristic for the infrared light, motion of the windows, which may lead to a distortion of the measured values, may occur as a consequence of a sudden change in pressure in the respiration circuit because of the small wall thickness, because the distance between the measuring gas sample holder windows varies. The measuring gas sample holder windows are provided with an outwardly arched side, which are fixed to the housing in the direction of the interior of the measuring gas sample holder. High-precision manufacture is necessary for manufacturing the measuring gas sample holder in order to avoid unevenness as a consequence of a projection of the measuring gas sample holder windows in the area of a duct in the interior of the measuring gas sample holder, which said duct is formed by the measuring gas sample holder windows and through which the patient's breathing air flows.

Furthermore, high requirements are imposed on the adhesive concerning biocompatibility.

A gas-measuring device operating according to the principle of infrared absorption for the continuous measurement of the $CO_2$ content in breathing gases, in which a sample holder tube consisting of a plastic transparent to infrared light is arranged replaceably in a bracket surrounding the sample holder tube, is known from U.S. Pat. No. 4,011,859 A.

WO 2004/081612 A describes a measuring gas sample holder, in which a ray path between a radiation source and an infrared radiation detector has a surface reflecting infrared light.

SUMMARY OF THE INVENTION

The object of the present invention is to provide a measuring gas sample holder, which can be manufactured in a simple manner and eliminates the above-described problems and drawbacks.

This object is accomplished according to the present invention by a measuring gas sample holder, comprising an inner part with two opposite walls, which limit the respiratory flow and which are transparent to infrared light, and an outer part with two opposite openings, which form a window each with the walls of the inner part, wherein the outer part surrounds the inner part and the inner part is thin-walled and an area of the inner part outside the windows is thermally fused together with the outer part.

The outer part is divided, furthermore, into an inlet area and an outlet area. The inlet area is designed as a connector for connection to a breathing tube leading to a patient and the outlet area is designed as a connector for connection to a breathing tube leading to a respirator.

The process according to the present invention for manufacturing the measuring gas sample holder has the following process steps: a) Manufacture of a thin-walled part with two opposite walls in a first step of an injection molding process, which forms an inner part of the measuring gas sample holder, b) introduction of a placeholder to keep away injection molded material from a first place and a second place that are to be kept free from injection molded material, at the opposite walls of the inner part, wherein the placeholder is aligned such that the first place to be kept free from material is flush with the second place to be kept free from material, and c) manufacture of an outer part of the measuring gas sample holder in a second step of the injection molding process, in which at least the inner part is completely extrusion coated with material, so that a thermal connection takes place between the two parts, wherein two opposite windows limiting the respiratory flow are formed at the sites of the placeholders.

The advantages gained with the present invention are especially that a highly cost-effective manufacturing process is made possible by the process according to the present invention for manufacturing the measuring gas sample holder. An additional operation for introducing the windows into the measuring gas sample holders is eliminated.

In a preferred embodiment, the inner part preferably consists of a random copolymer, as a result of which high transmission of infrared light is made possible, especially in a wavelength range of 4 µm to 5 µm.

Moreover, wall thicknesses of the inner part ranging from 170 µm to 210 µm can be obtained with the process according to the present invention for manufacturing the measuring gas sample holder, so that the windows formed by connecting the inner part to the outer part have good stability in case of pressure changes in the respiration circuit and motions as well as deformations of the windows can be avoided to the greatest extent possible.

The inner part of the measuring gas sample holder is preferably of a U-shaped design, such that the opposite walls are connected to one another via a web. However, a sleeve-like design of the inner part may also be provided in another embodiment. The inner part preferably extends over the measuring gas sample holder proper up into the inlet and/or outlet area of the outer part. Smooth surface of the duct, through which the patient's breathing air flows, is thus advantageously formed and turbulences as a consequence of unevenness in the duct are ruled out.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
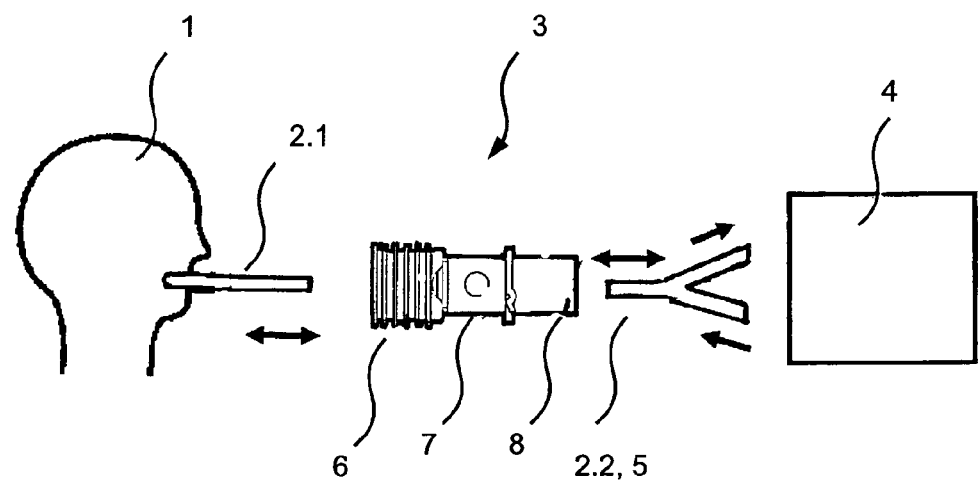
FIG. 1 is a schematic view showing a measuring arrangement of a mainstream process for measuring the concentration of gas components of the respiratory flow of a patient.

Referring to the drawings in particular, FIG. 1 shows a measuring arrangement of a mainstream method for measuring the concentration of gas components of a respiratory flow of a patient 1, for example, of $CO_2$. A measuring gas sample holder 3, through which the air inspired and expired by the patient 1, is connected between a respirator 4 supplying the patient 1 with breathing gas. The respirator 4 may comprise an anesthesia apparatus or a respirator. Infrared spectroscopy is preferably used for the measurement. A corresponding measuring device is provided at the measuring gas sample holder 3 and is not shown explicitly. The $CO_2$ concentration in the breathing gas flowing from and to the patient 1 can be continuously analyzed in this manner.

Figure 2:
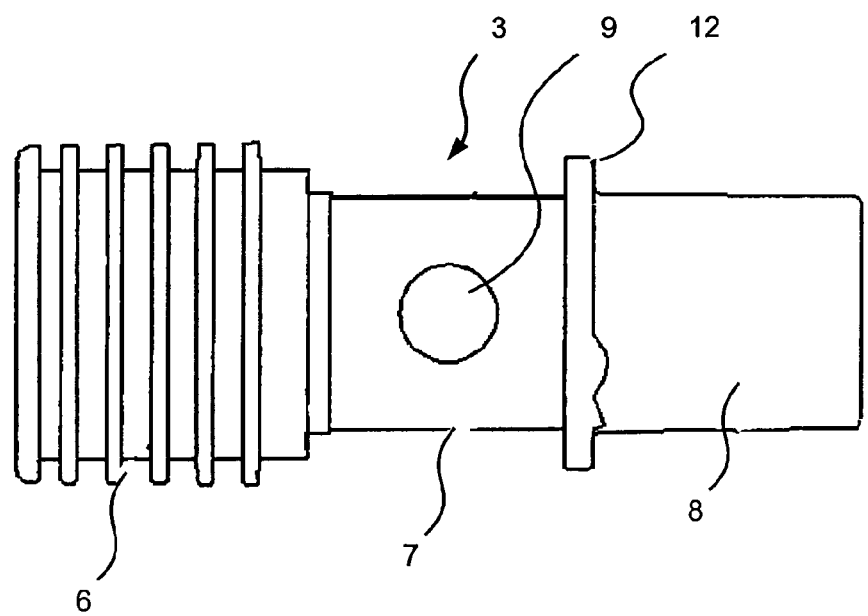
FIG. 2 is a side view in the longitudinal direction of the measuring gas sample holder according to the present invention.

FIG. 2 shows a side view of a measuring gas sample holder 3 according to the present invention. The measuring gas sample holder 3 comprises an inlet area 6, a middle area 7 and an outlet area 8. The inlet area 6 is preferably connected to a breathing tube 2.1 leading to the patient 1 (FIG. 1), whereas the outlet area 8 is coupled with the respirator 4 via the breathing tube 2.2. A so-called Y-piece 5, which splits the breathing air into an inspiratory part and an expiratory part, may also be provided between the outlet area 8 and the respirator 4. The inlet area 6 is conical and has grooves extending in parallel in the circumferential direction. The patient-side breathing tube 2.1 can be securely connected as a result to the inlet area 6 of the measuring gas sample holder 3. In addition, less material is needed for the manufacture of the inlet area 6 because of its shape. The inlet area 8 is likewise conical for secure connection to the device-side breathing tube 2.2 and to the Y-piece 5. To avoid confusion of the ports of the measuring gas sample holder 3, the diameter of the inlet area 6 is preferably larger than the diameter of the outlet area 8 in a preferred embodiment. In the middle area 7, the measuring gas sample holder 3 has two opposite windows 9, through which the infrared light is sent. One design of the windows 9 is shown in the sectional views in FIGS. 3 and 4. The windows 9 are formed from the thin-walled inner part 11 and from the outer part 10 surrounding the inner part 11, by two opposite walls 16 of the inner part 11, which said walls 16 limit the respiratory flow, and by two opposite openings of the middle piece 8 of the outer part 10. The measuring means, not shown, is positioned for the infrared spectroscopic measurement at a fastening means 12 such that an infrared light generated in an IR transmitter passes through the measuring gas sample holder 3 through the two windows 9. The infrared light is received in an IR detector unit, which is arranged opposite, is not shown more specifically and comprises an IR measuring detector with $CO_2$ filter, a reference detector with a corresponding filter and a beam splitter, and it is analyzed in an analysis unit, not shown in more detail. An analysis is performed on the basis of the absorption characteristic of the infrared light corresponding to the concentration of the CO2 gas in a spectral range specific of $CO_2$. A measurement is carried out especially at a wavelength of about 4.25 m to 4.3 m. The reference measurement by means of the reference detector is carried out with a wavelength at which $CO_2$ has no absorption. The concentration value of $CO_2$ in the breathing gas is determined from the measured values.

Figure 3:
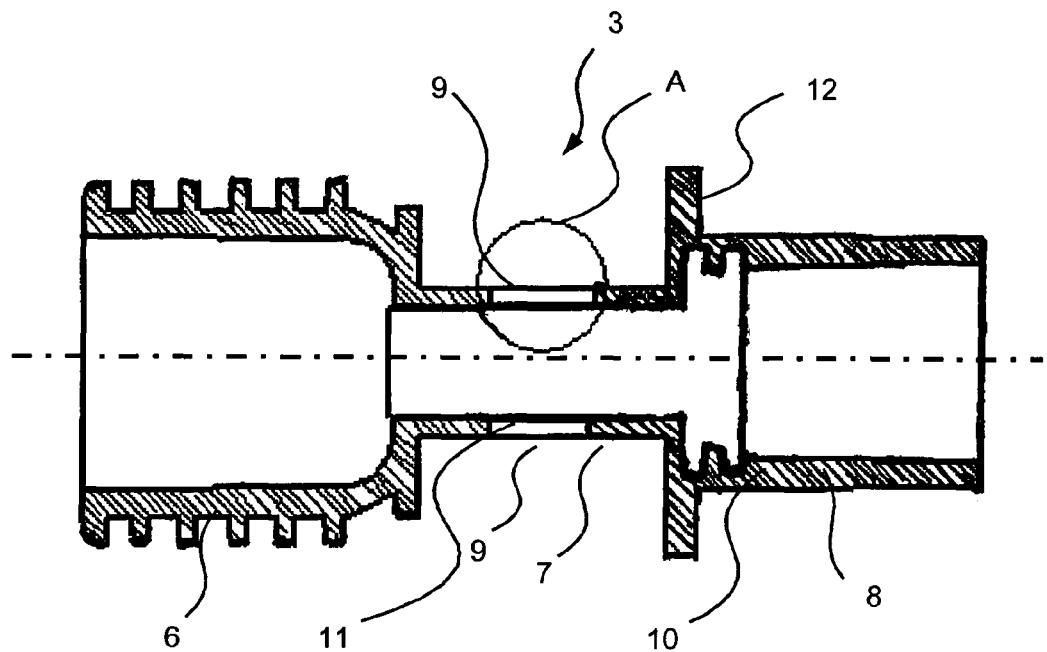
FIG. 3 is a sectional view of the measuring gas sample holder according to the present invention.
Figure 4:
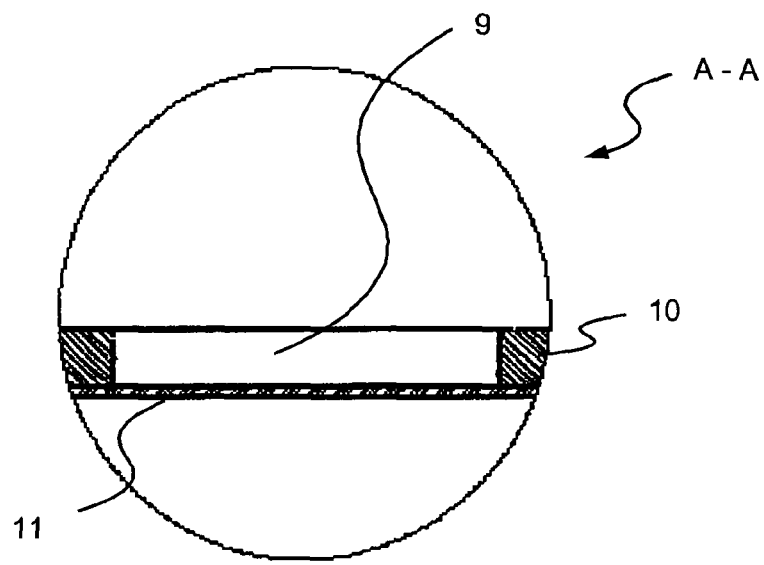
FIG. 4 is a schematic view showing a detail "A" of FIG. 3 on a larger scale.

The measuring gas sample holder 3 is designed in the embodiment shown in FIGS. 3 and 4 such that the inner part 11 extends into the inlet area 6 and/or the outlet area 8 of the outer part 10. A smooth surface of a duct of the measuring gas sample holder 3, through which duct breathing air of the patient flows, is thus generated with the thin-walled inner part 11, and turbulences of the breathing air as a consequence of obstacles in the duct are avoided. The windows 9 formed by the inner and outer parts 11, 10 are, on the one hand, very thin because of the thickness of the material of the inner part 11, which preferably equals 180 m, and they therefore offer high transmission of infrared light, and, on the other hand, sufficiently good stability and rigidity is brought about by the outer part 10 surrounding the inner part 11, so that deformations and hence erroneous measured values cannot occur in case of changing conditions of the breathing air. The breathing air duct of the measuring gas sample holder 3 is preferably cuboid in the middle part, whereas a cylindrical design is provided in the inlet area 6 and in the outlet area 8.

The mainstream measurement method is associated with an increase in the dead space not participating in the gas exchange. A larger volume must be applied per breath to compensate this dead space, i.e., the respiration pressure must be increased. However, an increased value of the respiration pressure may lead to damage to the not yet fully developed lungs over a longer period of time in newborns. Another embodiment of the measuring gas sample holder 3 according to the present invention therefore provides for a breathing air duct with a smaller cross section in order to reduce the dead space not participating in the gas exchange and to avoid damage to the lungs, especially in newborns and children.

Figure 5:
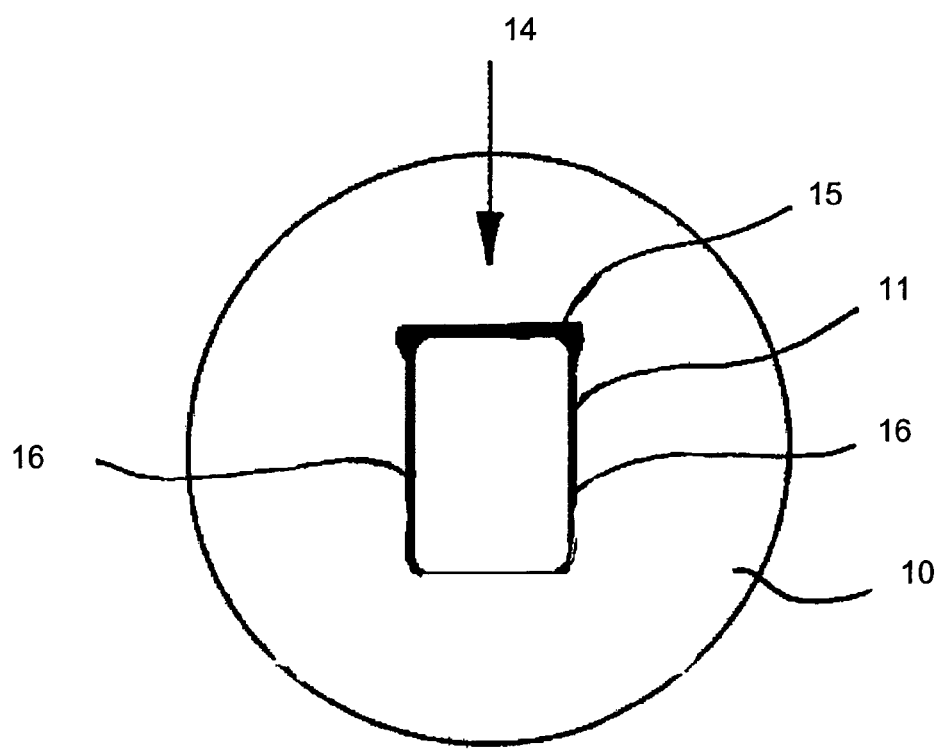
FIG. 5 is a cross sectional view through the middle part of the measuring gas sample holder according to the present invention in one embodiment.

The process of manufacturing the measuring gas sample holder 3 according to the present invention will be explained below on the basis of the exemplary embodiment shown in FIG. 5. FIG. 5 shows a cross section through the middle area 7 of a measuring gas sample holder 3, in which the inner part 11 is U-shaped, in such a way that the opposite walls 16 are connected to one another via a web 15 and the outer part 10 surrounds the inner part 11 and has two opposite openings, which are arranged at right angles to the direction of flow and form a window 9 each with the walls 16 of the inner part 11, which said walls 16 are connected via web 15. The measuring gas sample holder 3 according to the present invention is manufactured according to an injection molding process. A thin-wall part 11 with two opposite walls 16 is manufactured in a first process step in an injection mold, which forms the inner part 11 of the measuring gas sample holder 3. A feed point is provided centrally, above a web 15. Build-up of material in the web-side area of the inner part 11 is avoided hereby and the material can flow at the same time over the areas of the walls 16 to be prepared for the inner part 11 to be manufactured. Homogeneous structure of the opposite walls 16 of the inner part 11 can be achieved as a result. The homogeneity of the walls 16 prevents system-related measuring errors because of different transmission characteristics of the wall material of the walls 16. The injection molded material does not consequently have to pass through an entire injection mold, which is provided for manufacturing the outer part 10, but is distributed in an area only, which is necessary for manufacturing the opposite walls 16 of the inner part 11. Significantly reduced wall thicknesses can be obtained as a result. Additional tempering of the injection mold does, moreover, prevent premature cooling in the areas in which the injection mold is already filled completely with injection molded material.

A placeholder is provided in another process step to keep injection molded material away at the opposite walls 16 of the inner part 11 and it is aligned such that the place to be kept free from material is flush. Two areas are thus kept free from injection molded material at the opposite walls 16 of the inner part 11 and at least the inner part 11 is completely extrusion coated with material in a second step of the injection molding process, so that two opposite windows 9, which are arranged at right angles to the direction of flow and limit the respiratory flow, are formed at the sites of the placeholders. The material of the inner part 11 is now connected to the material applied by injection, which forms the outer part 10 of the measuring gas sample holder 3.

Thus, the measuring gas sample holder 3 is manufactured in an injection molding device in one part. The inner part 11 is injected at first in one piece with the process for manufacturing the measuring gas sample holder 3 according to the present invention and the outer body 10 of the measuring gas sample holder 3 is subsequently injected in the form of the outer part 10 around the inner part 11 and is thus thermally fused with the inner part 11. The inner part 11 is thus connected to the outer part 10 outside the windows 9.

While specific embodiments of the invention have been shown and described in detail to illustrate the application of the principles of the invention, it will be understood that the invention may be embodied otherwise without departing from such principles.

LIST OF REFERENCE NUMBERS

1 Patient
2.1 Breathing tube leading to a patient
2.2 Breathing tube leading to a respirator
3 Measuring gas sample holder
4 Respirator
5 Y-piece
6 Inlet area
7 Middle area
8 Outlet area
9 Window
10 Outer part
11 Inner part
12 Fixing means
14 Direction of flow of the injection molded material
15 Web
16 Walls of the inner part

The invention claimed is:

1. A measuring gas sample holder for measuring the concentration of gas components of a respiratory flow of a patient, the sample holder comprising:
    an inner part with two opposite walls limiting the respiratory flow, the walls being transparent to infrared light; and
    an outer part with two opposite openings, which each form a window with the walls of the inner part, wherein the outer part surrounds the inner part wherein the inner part is thin-walled and an area of the inner part outside the windows is thermally fused with the outer part.

2. A measuring gas sample holder in accordance with claim 1, wherein the inner part and the outer part are made of the same material.

3. A measuring gas sample holder in accordance with claim 1, wherein the inner part and the outer part are made of a material from the group comprised of the polyolefins.

4. A measuring gas sample holder in accordance with claim 1, wherein the wall thickness of the inner part is in the range of 170 m to 210 m.

5. A measuring gas sample holder in accordance with claim 1, wherein the inner part is U-shaped such that the opposite walls are connected to one another via a web.

6. A measuring gas sample holder in accordance with claim 1, wherein the inner part is of a sleeve-shaped design.

7. A measuring gas sample holder in accordance with claim 1, wherein a middle area of the outer part has means for fastening a measuring device.

8. A measuring gas sample holder in accordance with claim 1, wherein the outer part has an inlet piece and an outlet piece, wherein the inlet piece has grooves extending in parallel in the circumferential direction.

9. A measuring gas sample holder in accordance with claim 8, wherein the inlet piece and/or the outlet piece are conical.

10. A measuring gas sample holder in accordance with claim 1, wherein:
the outer part has an inlet piece and an outlet piece; and
the inner part extends into the inlet piece and/or the outlet piece (8) of the outer part.

11. A measuring gas sample holder in accordance with claim 1, wherein the inner part consists essentially of a random copolymer and the outer part consists essentially of an impact copolymer.

12. A process for manufacturing a measuring gas sample holder for the measurement of the concentration of gas components of the respiratory flow of a patient, the process comprising the steps of:
a) preparing a thin-walled part with two opposite walls in a first step of an injection molding process, which forms an inner part of the measuring gas sample holder;
b) introducing a placeholder to keep away injection molded material at a first area and at a second area of the opposite walls of the inner part, which said first and second areas are to be kept free from injection molded material, wherein said placeholder is aligned such that the first area to be kept free from material is flush with the second area to be kept free from material;
c) preparing an outer part of the measuring gas sample holder in a second step of the injection molding process, in which the inner part is completely extrusion coated with material, wherein two opposite windows limiting the respiratory flow are formed at the sites of the placeholders.

13. A process in accordance with claim 12, wherein the injection mold is designed such that a feed point is provided above a web in process step a) for preparing the inner part, said web connecting the two opposite walls.

14. A process in accordance with claim 13, wherein the feed point for preparing the inner part is arranged centrally in relation to the web.

15. A process of measuring the concentration of gas components of the respiratory flow of a patient, the process comprising the steps of:
providing a respirator or anesthesia apparatus;
providing a breathing tube leading to the patient; and
providing a sample holder connected between the respirator and the patient, wherein the sample holder comprises an inner part with two opposite walls limiting the respiratory flow with the walls being transparent to infrared light and an outer part with two opposite openings, which each opening forming a window with the walls of the inner part, wherein the outer part surrounds the inner part and wherein the inner part is thin-walled and an area of the inner part outside an area of the windows is thermally fused with the outer part wherein the walls in the area of the windows that is transparent to infrared light provides an infrared light passage for a measuring device, which determines the breathing gases, which flow to and from the respirator or anesthesia apparatus.

16. A process according to claim 15, wherein measuring is based on an infrared light absorption measurement.

17. A process according to claim 16, wherein the inner part and the outer part are made of a material from the group comprised of the polyolefins.

18. A process according to claim 16, wherein the wall thickness of the inner part is in the range of 170 m to 210 m.

19. A process according to claim 16, wherein the inner part is one of U-shaped such that the opposite walls are connected to one another via a web or sleeve-shaped.

20. A process according to claim 16, further comprising fastening device for fastening the measuring device, the fastening device being provided at a middle area of the outer part.

* * * * *